United States Patent [19]

Ricciardelli et al.

[11] Patent Number: 4,644,957

[45] Date of Patent: Feb. 24, 1987

[54] APPLICATOR STRUCTURE FOR BIOLOGICAL NEEDLE PROBES EMPLOYING SPIRAL-SHAPED RETAINING COILS

[76] Inventors: Robert H. Ricciardelli, 4240 Weise Rd., Carson City, Nev. 89701; John E. Shulze, 1450 Corte de Primavera, Thousand Oaks, Calif. 91360

[21] Appl. No.: 720,961

[22] Filed: Apr. 8, 1985

[51] Int. Cl.$^4$ .................................................. A61B 5/00
[52] U.S. Cl. .................................... 128/642; 128/639; 128/784; 128/786
[58] Field of Search .................... 128/419 P, 639, 642, 128/784–786

[56] References Cited

U.S. PATENT DOCUMENTS

| Re. 28,990 | 10/1976 | Hon et al. | 128/642 |
|---|---|---|---|
| 3,737,579 | 6/1973 | Bolduc | 128/785 |
| 3,750,650 | 8/1973 | Ruttgers | 128/642 |
| 3,827,428 | 8/1974 | Hon et al. | 128/642 |
| 3,986,497 | 10/1976 | Dali | 128/642 |
| 4,146,037 | 3/1979 | Flynn et al. | 128/419 P |
| 4,149,528 | 4/1979 | Murphy | 128/642 |
| 4,180,080 | 12/1979 | Murphy | 128/642 |
| 4,207,903 | 6/1980 | O'Neill | 128/785 |
| 4,235,246 | 11/1980 | Weiss | 128/419 P |
| 4,299,239 | 11/1981 | Weiss et al. | 128/785 |
| 4,301,806 | 11/1981 | Helfer | 128/642 |
| 4,320,764 | 3/1982 | Hon | 128/642 |
| 4,321,931 | 3/1982 | Hon | 128/642 |

Primary Examiner—William E. Kamm
Assistant Examiner—Mitchell J. Shein
Attorney, Agent, or Firm—Freilich, Hornbaker, Rosen & Fernandez

[57] ABSTRACT

A biological monitoring probe carrier incorporating a spiral retaining coil is easily put in place by a drive wrench passing through a guide channel with a longitudinal slot. Said channel holds the probe carrier near its distal end and holds a monitor cable alongside a shaft of the drive wrench which includes means for engaging the probe carrier to turn and advance it for the purpose of securing to tissue the retaining coil embedded in the distal end of the carrier. The proximal end of the wrench shaft includes a manipulating means for advancing the wrench a predetermined distance once the guide channel is placed against the tissue. The drive wrench is then withdrawn and the cable may then be released as the guide channel is withdrawn by allowing the cable to slip freely through the slot without need for disconnecting the monitor apparatus from the proximal end of the monitor cable.

10 Claims, 7 Drawing Figures

APPLICATOR STRUCTURE FOR BIOLOGICAL NEEDLE PROBES EMPLOYING SPIRAL-SHAPED RETAINING COILS

FIELD OF THE INVENTION

This invention relates to applicators for attaching and securing spiral-shaped, biological needle probes by remote manipulation to the surface of a living ogranism, or to an organ within a living organism, and more specifically to applicators for such probes applied to the human fetus via the transcervical route during labor and delivery.

BACKGROUND OF THE INVENTION

It is considered highly desirable by the obstetrician to monitor the viability of the fetus in-utero during the early and late phases of labor. At present, the most reliable methods of monitoring involve placement of a needle probe on the presenting part of the fetus; however, this procedure is technically difficult by direct manipulation during the early phases of labor because the cervix has not yet begun to dilate, necessitating the introduction of some type of narrow tubular applicator device into the birth canal such that the probe can be placed by remote external manipulation.

Various devices are known which may be used to facilitate the implantation of biological needle probes on an organ or fetus within a living body. A German Pat. No. 2,004,422 to Kresse in 1970 describes a long spiral electrode inserted through a hollow needle. The spiral is attached at its proximal end to a drive plunger. U.S. Pat. No. 4,000,745 to Goldberg describes a spiral electrode wound around a central needle used as an inserting tool for rapid placement of a pacemaker electrode in the human heart and U.S. Pat. No. 3,835,864 to Rasor describes a remote controlled device for screwing a retaining coil into the heart. The coil/carrier is rotated by a flexible drive tube inside a guide tube. A central retaining rod is coupled to the coil holder through a threaded end which operates to release the coil holder from the retaining rod after the coil is attached to the heart, using the drive tube to rotate the coil holder.

More to the point, numerous applicators have been deviced which are used specifically for the purpose of placing electrocardiogram electrodes on the human fetus while in the womb by traversing the birth canal after the onset of labor. Generally, these electodes are embedded in an insulating carrier assembly through which electrical wires or tubes are attached and, in the case where multiple electrodes are used, fixed spatial relationships between electrodes are maintained by virtue of such carrier mounting.

In U.S. Pat. Nos. 3,750,650 and 3,804,080 Ruttgers first proposed the combination of dual spiral "catcher" electrode(s) and a "counter" or reference electrode, disposed on a common insulating carrier, with two emanating electrical conductors which lead to external electrocardiogram monitoring equipment. An applicator device basically composed of two long concentric tubes, surrounding the emanating electrical conductors was disclosed which allowed for remote (i.e., external) manipulation and placement of the electrode/carrier assembly via a removeable intermating with the guide tube assembly. Remote twisting of the central tube, along with application of forward force was used to secure the electrodes.

The "Bipolar Electrode Structure For Monitoring Fetal Heartbeat and the Like" of Hon, et al., (U.S. Pat. No. Re 28,990) includes an applicator consisting of a "form-sustaining" guide tube through which a more flexible drive tube is advanced. The distal end of the drive tube has a "cooperating means" to engage the rear portion of the electrode disposed in the guide tube. Where a means for connecting an electrode to a monitor apparatus is needed, the signal leads are threaded through the common center of the drive and guide tubes from the electrode carrier assembly and ultimately exit at the proximal end of the drive tube. In a similar fashion to Ruttgers, a forward-twisting force is applied to the drive tube to effect placement of the electrode/carrier assembly, whereupon the drive tube and then the guide tube are pulled back and removed. The leads, having stripped wire on their proximal ends, are allowed to slip through the center of the guide and drive tubes, while remaining attached to the electrode/-carrier assembly which in turn is secured to the fetus. The leads are connected to the monitor apparatus, but only after completion of the insertion procedure and removal of the guide and drive tubes.

Neward (U.S. Pat. No. 3,910,271) discloses a "Method of Making a Bipolar Electrode Structure" yielding an application device similar to that of HON, but incorporating flexible guide and drive tubes and a moulded wire clamping device at the proximal end of the drive tube for the purpose of holding the drive tube and electrode/carrier assembly intimately in contact during the initial phase of insertion.

Dali (U.S. Pat. No. 3,956,497) similarly improved upon the invention of Hon by adding molded wire clamp at the proximal end of the drive tube.

Showell, et al., (U.S. Pat. No. 4,151,835) discloses "FETAL SCALP ELECTRODES" incorporating an integral applicator consisting of an arcuate needle and flexible drive shaft which secures the distal end of the device to the fetal epidermis and acts as a fetal electrocardiogram electrode. The proximal end of the drive shaft is external and incorporates a knob for engaging the needle and a centrally located pair of wires for interconnection to monitoring equipment.

Murphy (U.S. Pats. Nos. 4,149,528, and 4,180,080) discloses an "Electrode Assembly for Sensing Heart Activity" wherein the twisted, interconnecting electrode wires are rotated from their proximal ends to effect rotation of the electrode/carrier assembly. The wires travel through the center of a flexible guide tube. A safety stop and wire disengaging means are additional features of this invention.

Ferrar, et al, disclose "push-in" fetal electrode designs of a tuberous shape and applicators therefore in U.S. Pat. No. 4,244,375.

Helfer (U.S. Pat. No. 4,437,467) and Hon (U.S. Pat. No. 4,321,931) have disclosed revised carrier structures and mating applicators therefore which incorporate linear-to-rotary motion convertors with the objective of allowing the physician to place the spiral electrode by pushing on a plunger located at the proximal end of the applicator rather than pushing and rotating a drive tube.

In addition to the aforementioned inventions for monitoring of fetal electrocardiograms, several pH sensing electrodes have been conceived which incorporate spiral retaining coils for direct implantation into the fetus while in the womb. The "Electrode Cell Assembly" of Moller, et al (U.S. Pat. No. 3,973,555) does not describe an applicator means and presumably was inserted under direct manipulation. Ferrar, et al (U.S. Pat. No. 4,281,659) discloses an applying and securing means for fetal pH probe. First, large diameter guide and drive tubes are used to place a stable platform on the fetal epidermis secured by two spiral "catcher" needles. A lance mounted on a yet smaller tube is then advanced through the center of the drive tube to pierce the fetal epidermis. Finally the third tube is withdrawn and the cylindrical shaped pH probe is advanced through the center of the drive tube by attaching it to the end of a C-shaped channel. A total of five separate applicator parts are employed, not including the probe itself.

Finally, Bernard (U.S. Pat. No. 4,294,258) describes a "slanted-needle" pH probe with an integral applicator. The applicator employs two arcuate claws and an interconnecting cable which allows remote deployment of the claws. In an alternative embodiment, the pH probe is described as incorporated in two spiral-shaped hollow-needle electrodes on a common carrier but the applicator system is not described.

Each of the foregoing prior-art techniques of fetal probe application has its own drawback and limitation. Having not the aid of a guide tube to traverse the cervix, the devices of Showell and Bernard are difficult to apply during the early phases of labor. In addition, Ferrar's tuberous electrodes and applicators, as well as the devices of Kresse, Goldberg, and Moller, pose a risk of injury to the mother and/or fetus during the insertion procedure because needle structures that may penetrate tissue are exposed during transit of the birth canal.

And finally, the devices of Ruttgers, Rasor, Hon, Neward, Murphy, Helfer, and Ferrar (pH electrode applicator), although enjoying the relative safety and improved placement characteristic of employing a guide tube as part of the applicator, all suffer from a common drawback as related to the application of bioprobes employing spiral retaining coils. This drawback is that the monitor interconnecting cable, which conveys the probe signal from its location in situ to the external monitoring equipment, and which most commonly takes the form of wire(s), cable(s), or tube(s), must traverse laterally the hollow center of the guide and drive tube apparatus. This, in turn, means that the guide and drive tubes (which are necessarily small in diameter in order to transit the closed cervix) and which are withdrawn after placement of the probe/carrier assembly, and the proximal end(s) of the aforementioned wires, tubes, or cables—that connect to the monitor apparatus—must be necessarily of a diameter smaller than the guide and drive tubes.

This problem has been resolved in the prior art by use of stripped and tinned ends on the wires which, after probe insertion and applicator removal, are connected to a set of compression-type binding posts as a means of achieving a reliable signal connection to the monitor apparatus. While this type of connection achieves a reasonably inexpensive way of circumventing the diameter restriction placed on the proximal end of the monitor interconnecting cable, it places severe restriction on the types and complexity of signals which may be carried by the monitor interconnecting cable. For instance, where it is desired to connect more than 2 or 3 separate wires to the monitor apparatus, it is impractical to use bare-wire connections as described above because of the possibility of connecting the wires to the wrong posts.

In order to reduce connection time and confusion of multiple wires, it is desirable to use a cable connector, which for reasons of reliability and cost, typically has a maximum diameter which is larger than can be passed over by the guide and drive tubes.

Further, the bare-wire binding post type of interconnection, although suitable for electrical signals such as the 2-lead fetal electrocardiogram, is not useable where at least one of the signals being conveyed by the monitor interconnecting cable is transmitted light via a fiber optic cable, such as the spiral probes disclosed in FIG. 7 of copending U.S. patent application Ser. No. 685,154, and/or where the monitor interconnecting cable employs tubes for carrying fluids to or from the fetus, as disclosed by Ruttgers. For these latter types of spiral probes, operation is practical only with resort to cable-mounted fiber optic and/or fluid fittings (connectors) located at the proximal end of the monitor interconnecting cable.

A further disadvantage of the prior art of Ruttgers and others is that, as a result of the requirement that the guide and drive tube must be withdrawn over the proximal extremity of the monitor interconnecting cable, it is necessary to break the monitor interconnection while the guide and drive tubes are being withdrawn. This results in a temporary loss of monitoring information about the fetus, and in the case of certain probes which must be precalibrated prior to insertin (e.g., ion or gas sensing probes), breaking of monitor interconnections after insertion may result in a loss of probe calibration. From the foregoing it can be appreciated that it is highly desirable to conceive of a probe applicator device which allows the use of relatively large diameter cable connectors of various signal-carrying or fluid carrying types at the proximal end of the monitor interconnecting cable.

SUMMARY OF THE INVENTION

The present invention provides a simplified applicator device for tissue-penetrating needle probes which employ spiral-shaped retaining coils when such probes are applied by remote manipulation to the surface of a living organism (such as a fetus) or to an organ within a living organism. In addition, the present invention allows for: prior external calibration; placement of spiral probes; and simple and rapid removal of the applicator device, all without disconnection of the monitoring equipment from the proximal end of the monitor interconnecting cable. Further, the present invention allows for the use of various cable, tubing, or fiber optic connectors of unrestricted diameter to be utilized at the proximal end of the monitor interconnecting cable, if desired, for the accommodation of the heretofore mentioned types of sensors, when disposed in spiral retaining coil/carrier assemblies.

The illustrated embodiment of the invention includes a slotted guide channel with a C-shaped cross-section and of a suitable form to be comfortably inserted through the vagina and cervix of a woman in labor. A cylindrical-shaped insulating carrier, into which a hollow spiral retaining coil, rear-facing counter electrode, and the distal portion of a monitor interconnecting cable have been embedded, is rotatably and slidably disposed in the distal end of the guide channel. The hollow spiral retaining coil further serves as a fetal electrocardiogram electrode and as an outer housing for a fiber optical bioprobe. The monitor interconnecting cable exits the proximal surface of the carrier and is of a smaller diameter than the width of the longitudinal slot in the guide channel. The rear-facing counter electrode further serves as part of a cooperating engaging means which loosely mates with the distal end of a drive wrench.

The drive wrench incorporates at its distal end a cooperating engaging means comprised of transverse and longitudinal slots such that it mates loosely with the rear shape of the carrier/retaining coil/monitor interconnecting cable structure for the purpose of applying forward and circumferential force to the structure. The distal end of the drive wrench is connected to its proximal end via a long flexible shaft around which the monitor interconnecting cable is wound in a spiral of one counterclockwise turn, which prevents the monitor interconnecting cable from migrating transversely out of the guide channel while the wrench is in place. The proximal end of the drive wrench incorporates multistep-diameter cylinders. The smallest diameter cylinder incorporates a longitudinal slot or flute, which, with the aid of the inner surface of the guide channel is selected to entrap and engage the monitor interconnecting cable, such that the drive wrench and carrier/retaining coil assembly are maintained in close engagement and the retaining coil is held recessed within the distal end of the guide channel. The diameter of a middle cylinder is chosen to slide into the proximal end of the guide channel when the monitor interconnecting cable is released into the guide channel slot, such that the carrier/retaining coil assembly can be advanced and rotated into the fetal epidermis. The largest diameter cylinder serves as a handle for remote manipulation of the carrier/retaining coil assembly via the drive wrench, and further acts as a safety stop, when its forward face comes in contact with the proximal end of the guide channel, to limit the depth of penetration of the spiral retaining coil.

After seating of the retaining coil, the drive wrench is withdrawn by a rearward pulling until its distal end exits the proximal end of the guide channel. The guide channel is then withdrawn in a similar manner and the monitor interconnecting cable is allowed to slip freely out of the longitudinal slot in the guide channel.

The novel features of the invention are set forth with particuluarity in the appended claims. The invention will best be understood from the following description when read in conjunction with the drawings.

DESCRIPTION OF THE PREFERRED EMBODIMENTS

Figure 1:
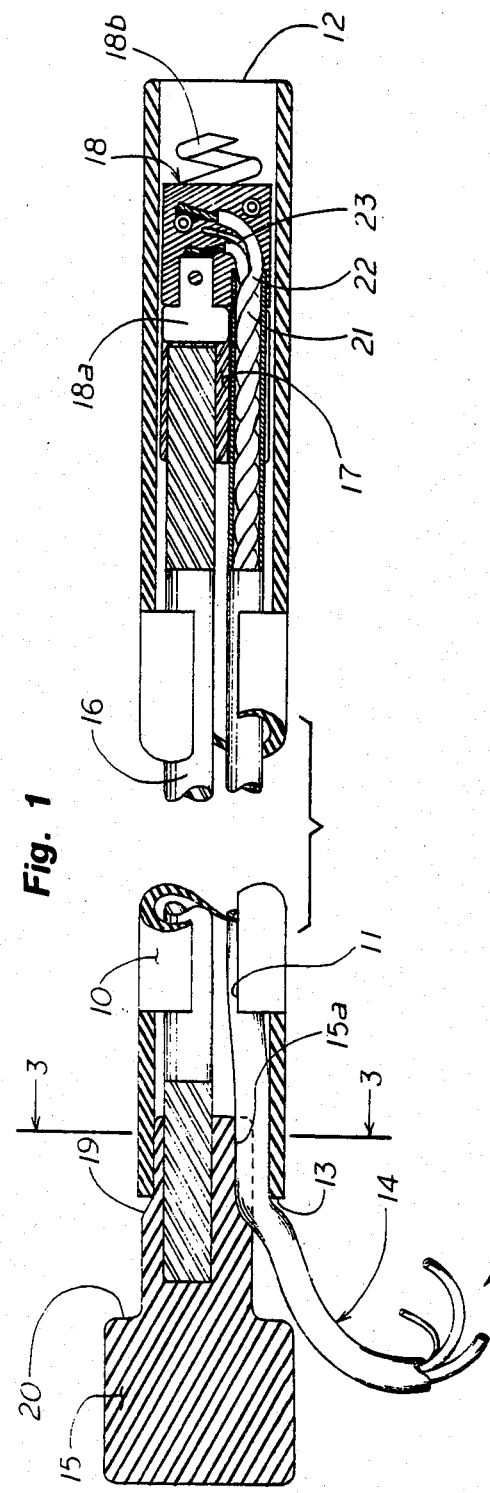
FIG. 1 is a longitudinal view of the preferred embodiment of the present invention with proximal and distal ends in center section.

With reference to FIG. 1, there is shown a guide channel 10 of C-shaped cross-section and having a longitudinal slot 11, an open distal end 12 and an open proximal end 13. A longitudinal slot is formed in the guide channel 10 of sufficient width for a monitor interconnecting cable 14 to be easily removed through the longitudinal slot 11, as best shown in FIGS. 5 and 6.

Figure 4:
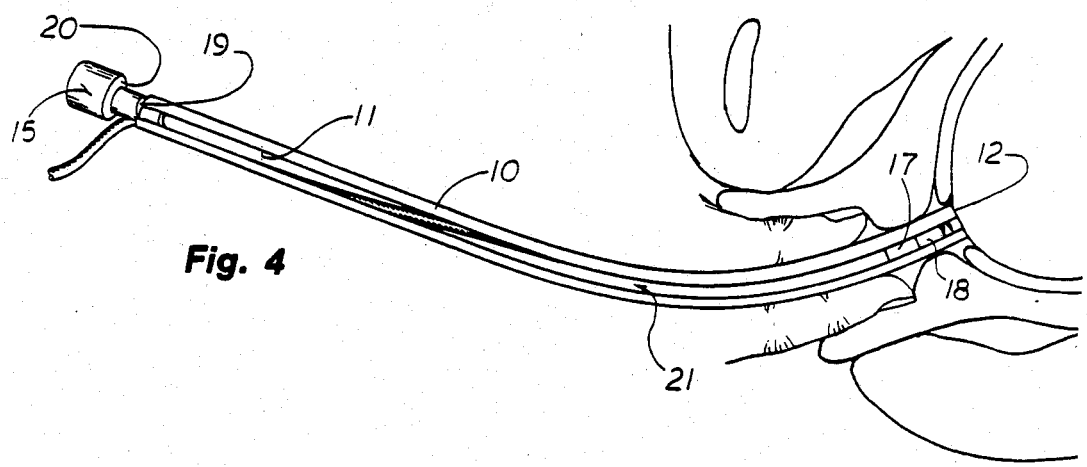
FIG. 4 is a perspective view illustrating insertion of the applicator with the distal end of the guide channel in contact with the fetus, but prior to release of the monitor interconnecting cable and subsequent placement of the retaining coil.
Figure 5:
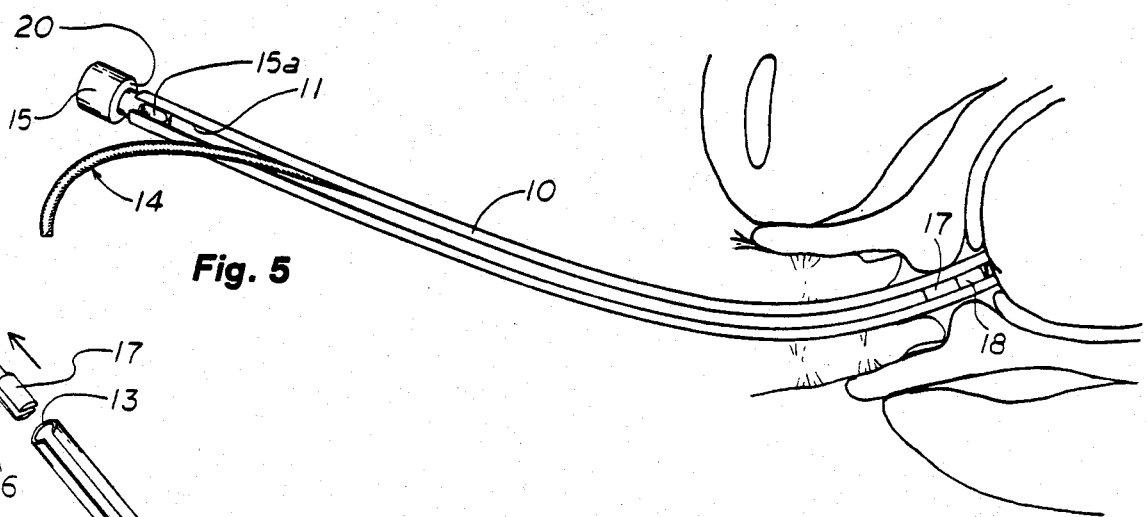
FIG. 5 is a perspective view illustrating placement of the retaining coil into the fetal epidermis.
Figure 6:
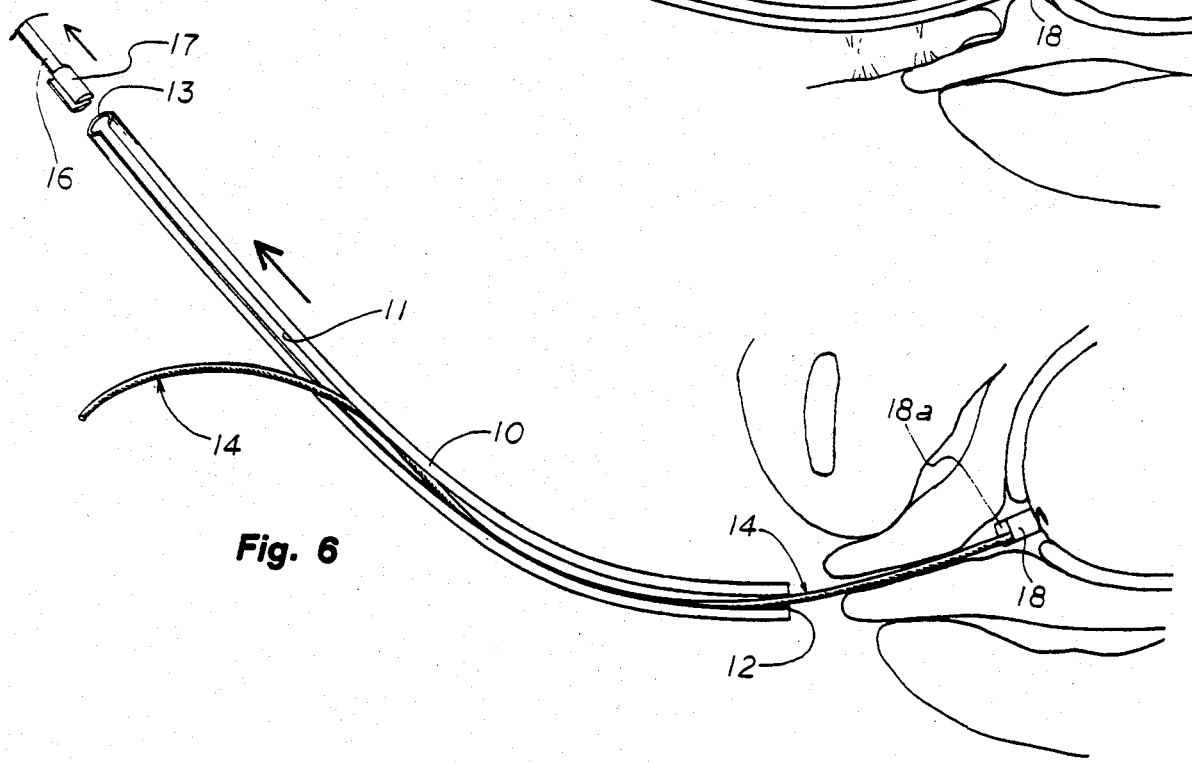
FIG. 6 is a perspective view illustrating removal of the drive wrench and guide channel after placement of the retaining coil.

In the preferred embodiment, the guide channel 10 is formed with a gentle curve, as best illustrated in FIGS. 4–6, such that the applicator conforms comfortably to the shape of the vagina and cervix of a woman in labor. However, the guide channel may also be straight, or of other forms, without departing from the spirit of the present invention. The guide channel is extruded and formed preferably from nylon.

Figure 2:
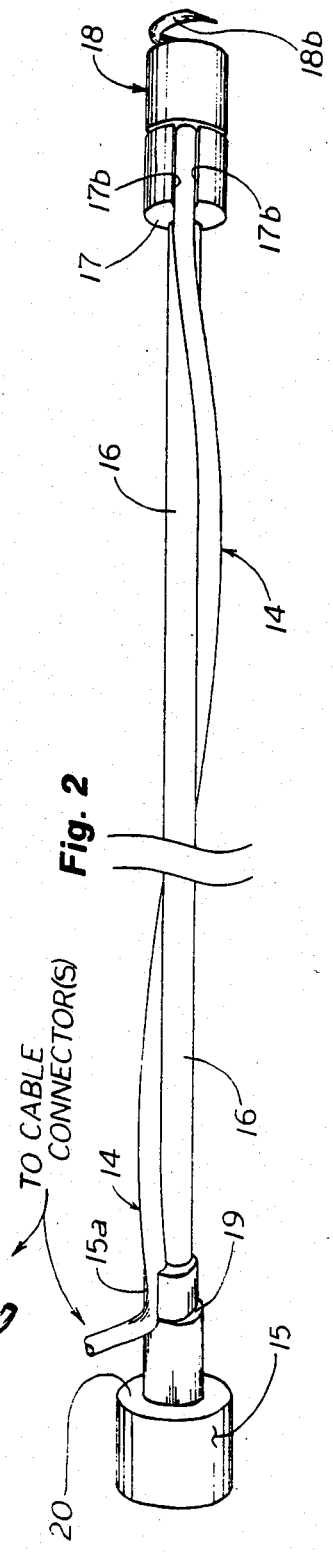
FIG. 2 shows perspective views of the proximal and distal ends of the intermating drive wrench and carrier/retaining coil/monitor connecting cable assemblies. The distal ends have been rotated one-fourth turn clockwise with respect to the proximal ends for clarity.

Also shown in FIG. 1 is a drive wrench, which extends very nearly the full length of the guide channel 10, and for clarity is described in three parts; a drive wrench proximal end 15; a drive wrench shaft 16; and a drive wrench cooperating engaging means 17, although it will be understood that these parts function as a unitary structure and are permanently bonded together, as is best shown in FIG. 2. The drive wrench proximal end 15 is constructed as three cylindrical sections of successively smaller diameter and length. The smallest cylinder is eccentric with respect to the next larger cylinder, such that the difference in diameters appears as a shoulder 19. The smaller cylindrical section of the proximal end 15 incorporates a longitudinal flute 15a, which, with the aid of the inner wall of the guide channel 10, traps and engages the interconnecting cable 14. The flute 15a is located at approximately 180 degrees around the cylinder with respect to the shoulder 19.

Approximately 50% of the diameter of the monitor interconnecting cable 14 is wedged into the flute 15a so that the monitor interconnecting cable 14 will rotate in unison with the drive wrench with respect to the guide channel 10. Thus, when the applicator is fully assembled, the drive wrench, monitor interconnection cable 14, and carrier/retaining coil assembly 18 are held firmly in the guide channel 10, and at a predetermined distance from the distal end 12, i.e., in a slightly recessed position relative to the distal end 12 of the guide channel 10, and are capable of rotating in unison with respect to the guide channel after overcoming the moderate resistance to rotation posed by the wedging of the monitor interconnecting cable 14 at the proximal end of the guide channel 10. Further, the drive wrench and carrier/retaining coil assembly 18 are prevented from moving forward by the wedging of the monitor interconnecting cable 14 and in addition by the shoulder 19 at the proximal end of the drive wrench. The next larger cylinder on the drive wrench proximal end of the guide channel 10 when the monitor interconnecting cable 14 has been released into the guide channel longitudinal slot 11 as best illustrated in FIG. 5. With the monitor interconnecting cable thusly released, the drive wrench can be advanced to its forward shoulders 20 of the largest cylinder. The maximum penetration depth of the retaining coil 18b is thus determined by selection of the longitudinal distance between shoulders 19 and shoulder 20, since this dimension determines the forward movement of the drive wrench and carrier/retaining coil assembly. The largest diameter section on the drive wrench proximal end 15 serves as a handle for remote manipulation of the carrier/probe assembly 18, and has a diameter of a convenient size for manual manipulation of the wrench assembly.

The drive wrench shaft 16 is of a diameter sufficiently smaller than the inside diameter of the guide channel 10 such that there is adequate clearance for the monitor interconnecting cable 14 to freely reside inside the guide channel in parallel to the drive wrench shaft. In the preferred embodiment, the monitor interconnecting cable 14 is wound in a spiral of one counterclockwise turn around the drive wrench shaft 16, as best illustrated in FIG. 2. While formed in a spiral around the drive wrench shaft, the monitor interconnecting cable 14 is retained securely inside the guide channel, even though its diameter is smaller than the longitudinal slot 11 in the guide channel 10, since the helix thus formed by the cable 14 around the drive wrench shaft 16 is larger than the slot width.

Figure 2A:
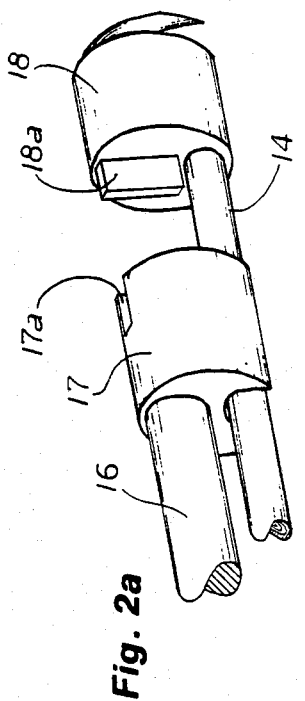
FIG. 2a is a perspective view of the distal end of the drive wrench assembly disengaged from the carrier/retaiing coil assembly.

The drive wrench shaft 16 is moderatley flexible, but capable of transmitting torque applied at the drive wrench proximal end 15 to the drive wrench cooperating engaging means 17. Said means contains a slot 17a shown in FIG. 2a that loosely engages an electrode 18a and a slot 17b shown in FIG. 2a for allowing passage of the monitor connecting cable 14. In the preferred embodiment, the cable exits the proximal surface of the carrier/retaining assembly 18 as an eccentric, as best illustrated in FIG. 2a, and the remaining portion of the diameter of the carrier along a chord which passes through the monitor interconnecting cable is occupied by a fin-shaped electrode 18a which also acts as at least part of the cooperating engaging means with respect to the distal end of the drive wrench cooperating engaging means 17.

Although the preferred form of the cooperating engaging means has been thus described as a slot 17a that fits over a fin-shaped counter electrode 18a, it will be understood that many other structures are possible such as square or hexagonal intermating parts, and the monitor interconnecting cable 14 need not exit the rear of the carrier/retaining coil assembly 18 eccentrically, but could instead by centered with respect to the proximal surface of the carrier 18 and one or more electrodes oriented in other portions, such as two in a cross, whereupon a mating drive wrench cooperating engaging means 17 can easily be constructed by one skilled in the art with two orthogonal slots at the distal end thereof.

Referring now to FIG. 2 in more detail, it shows the drive wrench assembly, comprising parts 15, 16, and 17 intermated with the carrier/retaining coil assembly 18 and the monitor interconnecting cable 14, as they are inserted into the channel 10. In the preferred embodiment, the cable is wound in a spiral of about one counterclockwise turn around the drive wrench shaft 16, as noted above. Although less desirable, the cable could also be installed without any spiral turn, in which the case it will run inside the guide tube parallel to the drive wrench shaft in a position about 90° from the slot 11 as illustrated in FIG. 3 which shows a cross section along a line 3—3 in FIG. 1 for the cable with or without a spiral turn.

Figure 3:
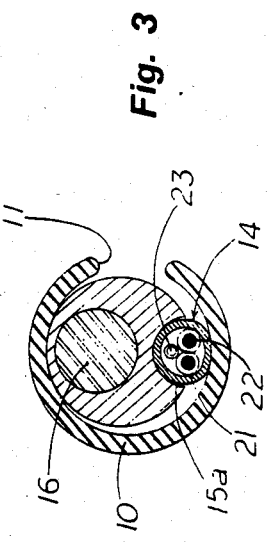
FIG. 3 is a tranverse section view taken in a plane 3—3 in FIG. 1.

Note in FIG. 3 that an approximately quarter-turn counterclockwise rotation of the drive wrench will result in release of the cable into the longitudinal slot 11 of the guide tube 10, whereupon a substantial reduction in frictional drag will occur. This quarter turn allows the obstetrician to release the cable in preparation for placement and advancement of the carrier/retaining coil assembly without the necessity to visually monitor the position of the monitor interconnecting cable 14 with respect to the longitudinal slot 11, since a tactile sensation of reduced rotational friction is felt when the cable is thusly released.

FIG. 4 illustrates the insertion of the assembled applicator through the vagina and cervix such that the distal end of the guide channel 12 is in contact with the fetus. Once that is achieved, the drive wrench proximal end 15 is rotated approximately one-fourth turn counterclockwise until a substantial reduction in drag force on the proximal end against the guide tube 10 occurs, at which time the monitor interconnecting cable has been released into the longitudinal slot 11, shown in FIG. 5.

As further shown in FIG. 5, the carrier/retaining coil assembly 18 can now be advanced and rotated into the fetal epidermis by applying forward force and approximately a one-turn clockwise rotation to the drive wrench proximal end 15 as the proximal end is advanced into the guide channel 10 the distance from the shoulder 19 to the shoulder 20. This attaches the probe to the scalp of the fetus and, in addition, the previously wound spiraling of the monitor interconnecting cable 14 around the drive wrench shaft 16 has been unwound so that the cable is now parallel to the shaft 16 and is free to exit the longitudinal slot 11.

The wrench is then easily removed by sliding it backward, as shown in FIG. 6. The guide channel is then removed by also sliding it back as the monitor interconnecting cable is allowed to drop free of the guide channel through the longitudinal slot 11, leaving the carrier/retaining coil assembly 18 secured to the fetus.

Although particular embodiments of the invention have been described and illustrated herein, it is recognized that modifications and variations may readily occur to those skilled in the art. For example, although electrical leads 21 and 22 and a fiber optic biosensor 23 are shown in the cable 14 in FIGS. 1 and 3 for use by probes on the carrier/retaining coil assembly 18, the carrier could also, or instead, include a tube for delivery or aspiration of fluids, and such a tube could be incorporated into a hollow retaining coil 18b. Also the retaining coil 18b may serve as a fetal electrocardiogram electrode, while the electrode 18a serves as a counter electrode. Still other electrical and/or fiber optic sensors may be embedded in the distal end of the carrier. Consequently, it is intended that the claims be interpreted to cover such modifications and variations.

What is claimed is:

1. Apparatus for application of a tissue-penetrating probe employing a spiral-shaped retaining coil comprising:

a guide channel with a longitudinal slot, said slot of a sufficient width to allow passage of a monitor interconnecting cable but of insufficient width to allow passage of an internally disposed cylindrically-shaped carrier/retaining coil assembly;

a cylindrically-shaped carrier slidably and rotatably disposed in the distal end of the guide channel; said carrier containing one or more monitoring means and having at least one spiral retaining coil embedded in its distal end, and a monitor interconnecting cable exiting the proximal end of said carrier and traveling longitudinally through said guide channel, said carrier also employing a cooperating engaging means on its proximal end for engagement and rotation by a drive wrench means;

a drive wrench means having a flexible, torque-transmitting shaft, said shaft being of sufficiently small diameter to allow parallel slidable residence of the monitor interconnecting cable in said guide channel; said drive wrench having a cooperating-engaging means at its distal end for engaging said carrier, and a manipulating means extending proximally from said guide channel for manual advancement and rotation of said shaft thereby to advance and rotate said carrier for the purpose of inserting the spiral retaining coil mounted on said carrier.

2. Apparatus is defined in claim 1, wherein said retaining coil also serves as an electrode.

3. The apparatus of claim 1, wherein said carrier also has embedded within its proximal surface a second electrode.

4. The apparatus of claim 1, wherein a flute of a depth less than the diameter of said cable is provided in said manipulating means and is used as a clamp for the monitor interconnecting cable while said flute is in a position to compress said cable against the inside wall of said guide channel, and said cable is released by rotating said flute in line with said longitudinal slot in said guide channel.

5. The apparatus of claim 1, wherein said wrench manipulating means has a first portion having dimension greater than the diameter of said guide channel, a second portion extending from said first portion having a diameter just enough smaller to fit into said guide channel, and a third portion extending from said second portion into said guide channel, said third portion having a diameter sufficiently less than the internal diameter of said guide channel to accommodate said cable in said guide channel while said third portion is in said guide channel, and means for causing said cable to rotate with said wrench manipulating means, whereby said portions of different diameters in the wrench manipulating means are employed to control the depth of penetration of the carrier/retaining coil assembly, and to align said cable with said slot for release of said cable, after which said wrench manipulating means may be advanced into said guide channel until said first portion abuts the proximal end of said guide channel.

6. Apparatus as defined in claim 5 wherein a flute of a depth less than the diameter of said cable is provided in said manipulating means and is used as a clamp for the monitor interconnecting cable while said flute is in a position to compress said cable against the inside wall of said guide channel, and said cable is released by rotating said flute in line with said longitudinal slot in said guide channel.

7. The apparatus of claim 1, wherein said monitor interconnecting cable is wound in a spiral of one counterclockwise turn around said drive wrench shaft.

8. The apparatus of claim 1, wherein said monitor interconnecting cable exits the proximal surface of the carrier as an eccentric to the center of that surface.

9. Apparatus as defined in claim 1 wherein said guide channel has a C-shaped cross section throughout its length.

10. Apparatus comprised of a wrench having a shaft, a carrier with a spiral retaining coil embedded in the distal end thereof, said carrier containing at least one biological monitoring means embedded therein with a cable attached thereto, a guide channel with a longitudinal slot to hold said probe carrier near the distal end thereof, and to hold said probe cable alongside said shaft, said slot having a width sufficient to allow passage of said cable, but of insufficient width to allow passage of said carrier, said shaft having means at its distal end for engaging said carrier while rotating and advancing it in said channel guide to the end thereof and having means at its proximal end for manually advancing and turning said shaft, whereby said carrier may be advanced and secured to tissue by said retaining coil and said cable may be released from said guide channel through said slot in order for said channel and shaft to be removed.

* * * * *